United States Patent [19]

Folkman et al.

[11] Patent Number: 4,795,703

[45] Date of Patent: Jan. 3, 1989

[54] HEPARIN ASSAY

[75] Inventors: Moses J. Folkman; Robert L. Hannan; Robert W. Thompson, all of Brookline; Robert S. Langer, Somerville, all of Mass.

[73] Assignee: The Children's Medical Center Corporation, Boston, Mass.

[21] Appl. No.: 837,517

[22] Filed: Mar. 7, 1986

[51] Int. Cl.$^4$ .......................... C12Q 1/56; C12Q 1/00
[52] U.S. Cl. ........................................ 435/13; 435/4; 435/810
[58] Field of Search ............... 435/4, 13, 232, 287, 435/288, 296, 810; 422/58, 61, 100; 128/763; 604/187

[56] References Cited

U.S. PATENT DOCUMENTS

| | | | |
|---|---|---|---|
| 4,067,777 | 1/1978 | Innerfield | 435/13 |
| 4,226,599 | 10/1980 | Butler et al. | 536/21 |
| 4,341,869 | 7/1982 | Langer | 435/232 |
| 4,373,023 | 2/1983 | Langer et al. | 435/2 |

OTHER PUBLICATIONS

Klein et al, J. Lab. Clin. Med., 102(5): 828–837, Nov. 1983, "Use of Heparinase to Eliminate Heparin Inhibition in Routine Coagulation Assays".
Nash et al, Anal. Biochem., 138:319–323 (1984), "Determination of Plasma Heparin by Polybrene Neutralization".
Efimor et al, Chemical Abstracts, 101:3553x, 306 (1984).
Jakoby, *Methods in Enzymology–Enzyme Purification and Related Techniques,* vol. XXII Academic Press, New York, 23–49 (1971).
Hattersley, 1966, J.A.M.A., vol. 196, p. 436.
Bull et al., 1975, J Thorac. Cardiovasc. Surg., vol. 69, p. 685.
Klein et al., 1982, Anal. Biochem., vol. 124, p. 59.
Hutt et al., 1972, J. Lab. Clin. Med., vol. 79, p. 1027.
Langer et al., 1982, Science, vol. 217, p. 261.
Ellison et al., 1974, J. Thorac. Cardiovasc. Surg., vol. 67, pp. 723–729.
Horrow, 1985, Anest. Analg., vol. 64, p. 348.
Sharath et al., 1985, J. Thorac. Cardiovac. Surg., vol. 90, p. 86.
Yang et al., 1985, J. Biol. Chem., vol. 260, p. 1849.

*Primary Examiner*—Esther M. Kepplinger

[57] ABSTRACT

The level of heparin in a blood sample is measured by measuring the clotting time of two aliquots of the blood sample, using standard clotting assays, with one of the aliquots being firstly treated with a heparin-degrading compound, such as heparinase. The difference in clotting times is a direct measure of the heparin concentration in the sample.

4 Claims, 1 Drawing Sheet

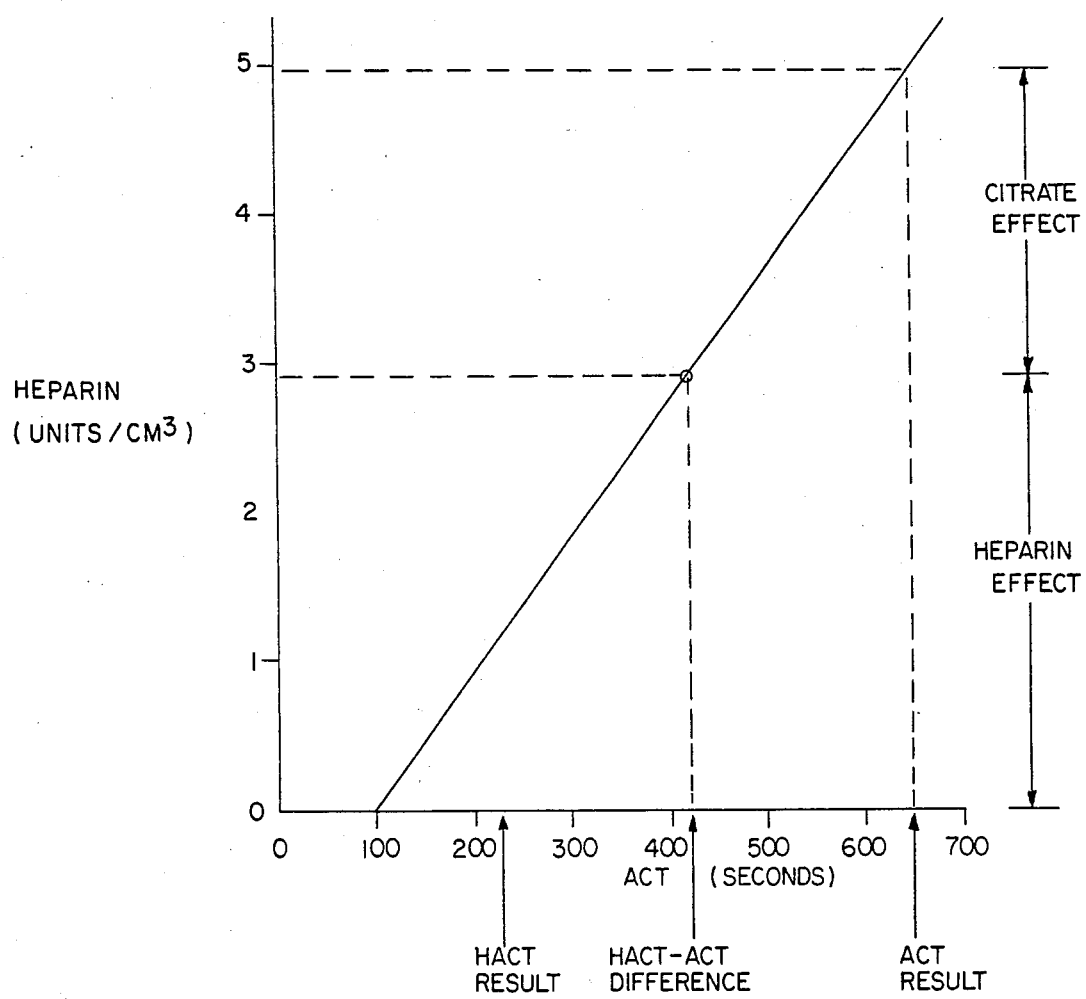

HEPARIN ASSAY

BACKGROUND OF THE INVENTION

The invention relates to a specific method for the assay of heparin.

Heparin is an inhibitor of the thrombin-fibrinogen blood clotting system and is used in patients undergoing procedures in which the prevention of clot formation is important, for example, patients undergoing extracorporeal blood circulation and/or treatment.

The level of heparin in whole blood can be measured in a number of ways, the simplest being a measurement of the activated clotting time (ACT), (Hattersley, 1966 J.A.M.A. 196:436). This method measures the time that it takes for blood, treated with diatomaceous-earth, to clot. There is a straight line relationship between the amount of physiologically active heparin in the blood and the delay in the time taken for a clot to form (Bull et al. 1975, J. Thorac. Cardiovasc. Surg. 69:685). Most types of cardiac surgery currently performed, including about 400,000 coronary bypasses per year in North America, require high levels of heparinization of the patient and an extracorporeal oxygenation circuit during cardiopulmonary bypass. Heparin reversal is routinely carried out with intravenous protamine sulfate at the end of the procedure, and the patient's coagulation status is followed by monitoring the activated clotting time. A number of complications with the use of protamine have been described, including fatal reactions. Heparin reversal is not always complete by this method, and may require additional protamine in the intensive care unit; the phenomenon of "heparin-rebound" has also been described where heparin activity is mobilized from fat stores during rewarming of the patient in the hours following surgery, and may contribute to excess bleeding during this period. A second method entails the chemical measurement of heparin. this method makes use of the chromophore, azure A (Klein et al., 11982, Anal. Bioc. 124:59). Unlike physiological assays this chemical assay is not affected by the presence of other anticoagulants, but detects both physiologically and non-physiologically active fragments of heparin and so is not adequate for managing heparin and protamine therapy during or after extracorporeal circulation or treatment of blood.

The analysis of certain other factors affecting blood clotting has been described by Hutt et al. 1972, J. Lab. Clin. Med. 79:1027, where partially purified heparinase was added to plasma samples prior to performance of the prothrombin and partial thromboplastin times. Elimination of the heparin effect was demonstrated for these coagulation tests, but the use of the enzyme was not extended to any other measures of coagulation status. The authors conclude their paper with the statement:

"The availability of this reagent will make possible the detailed investigation of coagulation mechanisms in severely ill, hospitalized patients receiving heparin therapy. Specific clinical situations in which the use of heparinase would be useful are: (1) the patient with disseminated intravascular coagulation already being treated with heparin; and (2) the patient with myocardial infarction or venous thromboembolic disease being changed from heparin to coumadin therapy. It is entirely possible that a standardized amount of heparinase could be added to commercially available coagulation assay reagents on a routine basis, thus avoiding inaccuracies resulting from unsuspected plasma contamination with heparin."

The coagulation tests and the methods described in this report are not applicable to the needs of cardiovascular surgery. Heparinase has also been used for the deheparinization of blood before it is returned to a patient (Langer et al., 1982, Science 217:261).

Although the heparin-ACT does-response method has markedly improved heparin and protamine therapy in cardiovascular surgery, certain problems remain. Despite complete heparin reversal at the end of the surgical procedure, some patients develop heparin-related coagulation defect in the early (up to 8 hours) postoperative period, referred to as "heparin rebound" (Ellison et al. 1974 J. Thorac. Cardiovasc. Surg. 67 723–729.). The ACT will be prolonged, and specific therapy requires more protamine. On the other hand, cardiopulmonary bypass and extracorporeal circulation may induce a number of secondary coagulation defects that are not heparin-related. Such defects may be caused by hemodilution, hypothermia, platelet disorders, disseminated coagulation, or fibrinolysis, and they may appear as a bleeding tendency in the operating room or in the postoperative period. Because the ACT is prolonged by these disorders, the bleeding tendency may be attributed to heparin; however, these secondary coagulation defects are not protamine-reversible. Specific and rapid determination of heparin activity is not available, and most patients are treated in a "shotgun" manner with protamine and blood products in this situation. The well known risks of protamine treatment make specific identification of secondary coagulation defects a highly desirable aim.

SUMMARY OF THE INVENTION

In one aspect the invention features a method for the rapid specific measurement of active anticoagulant heparin in a blood sample. The method comprises dividing the sample into two or more aliquots and adding a heparin-degrading compound, preferably herparinase, to one of these. The clotting time of each aliquot is then measured in the usual manner, for example as whole blood clotting tissue or as activated clotting time, and the difference in time between the two samples represents a measure of the level of heparin in the blood sample.

In the preferred embodiments the heparinase used in the assay is purified, e.g. by dialysis, and lyophilized, and the clotting time is measured as the activated clotting time (ACT).

In a second aspect the invention features a test kit, for determining the level of heparin in a blood sample, which comprises a system containing a purified heparin-degrading compound, preferably heparinase. In the preferred embodiments the system is a syringe, test tube, bead or a machine capable of aliquoting the heparinase.

The assay method of the present invention for heparin is specific to physiologically active heparin. That is, the assay measures only the presence of heparin that affects blood clot formation. Such a measurement allows a precise calculation of the amount of an agent, such as protamine, for the neutralization of the heparin. Previous assays give overestimates of the amount of physiologically active heparin and thus may guide a physician to inject too great an amount of protamine, which may even be lethal (Horrow, 1985, Anest. Analg. 64:348; Sharath et al., 1985, J. Thorac. Cardiovac. Surg. 90:86). The assay method is rapid and can be easily performed, at the bedside or in an operating room, by nurses or perfusionists, using a conventional readily available machine for determining clotting times. The assay also enables the physician to determine the level of other non-heparin blood clotting factors and to plan his treatment of these.

Other features and advantages of the invention will be apparent from the following description of the preferred embodiments and from the claims.

DESCRIPTION OF THE PREFERRED EMBODIMENTS

The drawing is a graphical representation of the results of activated clotting time (ACT) tests with or without heparinase treatment.

Blood samples may be obtained by any standard means. Measurement of the amount of any factors affecting the rate of blood clotting, in these samples, can be made by any standard method, for example whole blood coagulation time, (WBCT), or activated clotting time (ACT) in both of which the measurement bears a linear relationship to the heparin concentration (Young, 1982, In Utley (ed) Pathophysiology and techniques of cardiopulmonary bypass, Vol. 1. Willimas and Wilkins, Baltimore pp. 88–105). Each assay should firstly be standardized, for example, in the WBCT and ACT tests, to determine the relationship and the time limits at which the linear relationship holds true. For the ACT test this is between 100–600 seconds.

In order to degrade heparin within a blood sample any enzyme, or other degrading reagent which is specific to heparin, may be used. Preferably the enzyme, heparinase, isolated from *Flavobacterium heparinum* is used. This enzyme may be readily isolated in partially purified form by the standard procedures described by Yang et al. (1985, J. Biol. Chem. 260:1849). Briefly, this entails purification of the enzyme by hydroxylapatite chromatography, gel filtration chromatography, and chromatofocusing. Preferably the enzyme is then further purified by being dialyzed three times against an excess of distilled water, frozen at $-20°$ in 1 cm$^3$ (0.2–0.4 mg protein/cm$^3$) aliquots for 6–24 hours, and lyophilized in vacuo. Such enzyme preparations can be stored at 0° C. for upwards of 6 weeks. In one embodiment the enzyme may actually be lyophilized within a 3–5cm$^3$ syringe, which serves as a package or container and which may later be used to obtain a blood sample. The amount of heparinase used is not critical, so long as it is in excess of the amount required for degradation of the maximum amount of heparin present in the sample being assayed. In general, 10–50 units (30–150 μg of protein) of purified heparinase for each 2 ml sample of blood is adequate. (One unit of heparinase degrades one mg of heparin per hour at 37° C.; one mg of heparin having 150 units of heparin activity.)

The assay for heparin involves simultaneously performing a standard blood clotting test on two aliquots of a blood sample. Before or during this test one of the two aliquots must be treated with heparinase. The difference between the two measurements is a direct measure of the amount of heparin in the blood sample, and the precise amount of heparin can be estimated from a standard curve, as shown in the drawing.

Treatment with heparinase involves gently mixing a blood sample with an excess of heparinase, in solid form or in solution. For example, an assay kit may be provided which includes a syringe containing heparinase powder; the blood sample may be sucked into the syringe, and the syringe inverted gently for ten seconds. This process can be performed at room temperature (15°–25° C.).

EXAMPLE

Whole human blood, from eight volunteers, was heparinized ex-vivo with three units of heparin per cm$^{-3}$ and kept at 37° C. An ACT test was performed on a 2 cm$^3$ aliquot of each blood sample and, at the same time, a 2 cm$^3$ aliquot of each blood sample was drawn into a syringe containing 162 μg (47 units) of dialyzed and lyophilized heparinase, mixed by gently inverting the syringe for ten seconds, and an ACT test performed on the sample (the HACT test). The ACT and HACT tests were performed using a Hemochron 400 apparatus (International Technidyne Corp.). The results are shown below:

| Test Blood | 1 | 2 | 3 | 4 | 5 | 6 | 7 | 8 | MEAN & S.D. |
|---|---|---|---|---|---|---|---|---|---|
| ACT control | 93 | 101 | 92 | 111 | 107 | 112 | 94 | 102 | 101.5 +/− 8.0 |
| HACT control | 113 | 86 | 99 | 100 | 87 | 126 | 95 | 98 | 100.5 +/− 13.3 |
| ACT heparin | 701 | 798 | 459 | 652 | 404 | 517 | 643 | 638 | 601.5 +/− 131.2 |
| HACT heparin | 118 | 118 | 115 | 116 | 116 | 130 | 102 | 115 | 116.2 +/− 7.8 |

The ACT and HACT controls contained no heparin and gave similar results in the ACT test. In contrast, the heparin-containing samples, without heparinase treatment, showed greatly prolonged clotting times. After heparinase treatment these samples had clotting times which were much lower, but greater than the controls. The difference between the HACT control results and the HACT heparin results may reflect the presence of non-heparin blood clotting factors.

In order to determine the specificity of the HACT test the above assay was repeated with the addition of citrate to some tubes. An excess of citrate (15 mg) was added to each tube and the blood then partially recalcified with 1 ml of 0.1% CaCl$_2$, to provide a partial but measureable coagulation defect. This addition simulates a lack of calcium in the blood, and is unrelated to the level of heparin. A characteristic result is shown below:

| ACT control | ACT citrate | ACT citrate/ heparin | HACT citrate/ heparin |
|---|---|---|---|
| 98 sec | 216 sec | 653 sec | 299 sec |

These results show that the presence of citrate in the blood increases the ACT result, even in the absence of heparin. The HACT test overcomes this problem since the level of heparin is determined as the difference between the ACT and HACT results, i.e. 424 (653−229) secs. This figure can be used as an accurate measure of heparin level. Note that the assay results were obtained rapidly (within 11 minutes)—a critical factor when treatment to remove heparin may be required.

The results of the above assay are shown in the drawing. The solid line represents a standard curve estimated from assays performed to relate the HACT/ACT test result to heparin concentration. In the above citrate assay the ACT result was 653 seconds. If a physician regarded this value as representative of actual heparin concentration then he would add an equivalent amount of protamine (5 units) to neutralize the heparin. The HACT result gave a value of 229 seconds, the difference being 424 seconds (shown as solid circle on the drawing). This value corresponds to a considerably lower amount of heparin (3 units) in the blood. Thus without the HACT result the physician would add an almost 70% excess of protamine, possibly compromising the patient. This overestimation of heparin concentration would be repeated, if the results of later ACT tests are used to estimate heparin concentration, since the addition of even an excess of protamine will not bring the ACT value to a normal level when its elevated level is not caused by heparin but by other factors which are not removed by protamine. The HACT test allows the physician to specifically treat the heparin-caused effect and to be aware of the non-heparin effect.

This assay is of use to physicians treating many patients, particularly children, suffering from complications of systemic anticoagulation during haemodialysis, extracorporeal membrane oxygenation, and cardiopulmonary bypass. It is also of use in any other situation in which it is important to know the level of heparin.

The heparinase need not be used as a lyophilized powder within a syringe but can be used in solution as a liquid and in a kit comprising any readily available apparatus or system such as test tubes, or even automated machines which can dispense the enzyme as required; similarly the enzyme can be immobilized onto beads or filters and used in this form to treat blood samples before the ACT/HACT test. The simultaneous measurement of blood clotting times of heparinase-treated and -untreated samples is not essential but gives more accurate results than if the measurements are made some time apart. Similarly, the heparinase can be added at the time of measurement rather than immediately prior to measurement of the blood clotting time.

Other embodiments are within the following claims.

What is claimed is:

1. A method for the specific measurement of heparin in a blood sample comprising:

dividing said sample into at least two aliquots, adding heparinase to a first said aliquot, measuring the clotting time of said first aliquot and of a second aliquot free from heparinase and determining the difference between the clotting time of said first and second aliquot as a measure of the amount of heparin in said blood sample.

2. The method of claim 1 wherein said heparinase is dialyzed against distilled water and lyophylized before adding to said first aliquot.

3. The method of claim 1 wherein said clotting time is measured as the activated clotting time or the whole blood coagulation time.

4. The method of claim 3 wherein said difference is determined within 11 minutes.

* * * * *

UNITED STATES PATENT AND TRADEMARK OFFICE
CERTIFICATE OF CORRECTION

PATENT NO. : 4,795,703

DATED : January 3, 1989

INVENTOR(S) : Moses J. Folkman, et al.

It is certified that error appears in the above-identified patent and that said Letters Patent is hereby corrected as shown below:

An additional assignee should be listed in the heading:

--Massachusetts Institute of Technology, Boston, Mass.--

Column 1, Line 38: "this method" should be --This method--

Column 3, Line 53: "in vacuo" should be --*in vacuo*-- (italicized)

Signed and Sealed this

Fifteenth Day of August, 1989

*Attest:*

DONALD J. QUIGG

*Attesting Officer*   *Commissioner of Patents and Trademarks*